(12) United States Patent
Murch et al.

(10) Patent No.: US 10,182,777 B2
(45) Date of Patent: Jan. 22, 2019

(54) OPEN DRUM GANTRY FOR COMPUTED TOMOGRAPHY SYSTEM

(71) Applicant: Morpho Detection LLC, Newark, CA (US)

(72) Inventors: Anthony James Murch, Hayward, CA (US); Jared William Moore, Oakland, CA (US); Pedro Andres Garzon, Santa Clara, CA (US); Samit Kumar Basu, Fremont, CA (US)

(73) Assignee: MORPHO DETECTION, LLC, Newark, CA (US)

( * ) Notice: Subject to any disclaimer, the term of this patent is extended or adjusted under 35 U.S.C. 154(b) by 361 days.

(21) Appl. No.: 15/049,671

(22) Filed: Feb. 22, 2016

(65) Prior Publication Data

US 2017/0238889 A1    Aug. 24, 2017

(51) Int. Cl.
*A61B 6/00* (2006.01)
*H05G 1/10* (2006.01)
(Continued)

(52) U.S. Cl.
CPC ............ *A61B 6/4435* (2013.01); *A61B 6/032* (2013.01); *A61B 6/035* (2013.01); *A61B 6/56* (2013.01); *G01N 23/046* (2013.01)

(58) Field of Classification Search
CPC ....... A61B 6/032; A61B 6/4435; A61B 6/027; A61B 6/035; A61B 6/56; A61B 6/4441; A61B 6/542; A61B 6/06; A61B 6/4085; A61B 6/5205; A61B 6/4035; A61B 6/4488; A61B 6/4233; A61B 6/541; A61B 6/545; A61B 6/0457; A61B 6/14; A61B 6/466; A61B 6/488; A61B 6/4078; A61B 6/508; A61B 6/5258; A61B 6/547; A61B 5/0066; A61B 5/0073; A61B 5/0084;
(Continued)

(56) References Cited

U.S. PATENT DOCUMENTS 4,644,573 A    2/1987  Palermo et al.
4,969,171 A *  11/1990  Yamada ................... A61B 6/56
                                                        378/101

(Continued)

FOREIGN PATENT DOCUMENTS

DE    102013205606 A1    10/2014
EP        2688078 A1     1/2014
JP       2007037873 A    2/2007

OTHER PUBLICATIONS

Extended European Search Report in connection with with European Patent Application No. 17000256.2, dated Jun. 7, 2017, 7 pgs.

*Primary Examiner* — Irakli Kiknadze
(74) *Attorney, Agent, or Firm* — Armstrong Teasdale LLP

(57) ABSTRACT

A gantry rail for a gantry computed tomography (CT) system includes a secondary side of a rotary transformer and an annular body having an annular rolling surface and an annular slip ring surface. The annular body is aligned orthogonal to a longitudinal axis of the gantry CT system. The annular rolling surface has a normal vector that extends radially outward and orthogonal to the longitudinal axis. The annular slip ring surface defines a plane orthogonal to the longitudinal axis, and includes a slot disposed in the slip ring surface. The slot is configured to engage the secondary side of the rotary transformer.

19 Claims, 9 Drawing Sheets

(51) Int. Cl.
*G01N 23/046* (2018.01)
*A61B 6/03* (2006.01)

(58) Field of Classification Search
CPC ... A61B 5/02007; A61B 8/0891; A61B 6/037; A61B 6/4014; A61B 6/0421; A61B 6/08; A61B 6/405; A61B 6/482; A61B 6/505; A61B 6/548; A61B 6/583; A61B 18/1815; A61B 2018/00577; A61B 18/18; A61B 18/1233; A61B 18/1492; A61B 2018/00023; H05G 1/10; H05G 1/08; H05G 1/12; H05G 1/20; H05G 1/34; H05G 2/003; H05G 2/005; H05G 1/66; H05G 1/06; H02J 50/10; H01F 38/18; H01F 30/16; H01F 27/245; H01F 38/14; H01F 3/02; H05H 1/06; H02M 7/515; H02M 7/10; H04B 2203/5425; H04B 2203/545; H04B 2203/5483
USPC .......... 378/4, 15, 19, 62, 101–107, 114–119
See application file for complete search history.

(56) References Cited

U.S. PATENT DOCUMENTS

| | | |
|---|---|---|
| 5,018,174 A | 5/1991 | Collins |
| 5,208,581 A | 5/1993 | Collins |
| 5,608,771 A | 3/1997 | Steigerwald et al. |
| 5,784,428 A | 7/1998 | Schmidt |
| 5,799,057 A | 8/1998 | Hoffman et al. |
| 6,459,757 B1 | 10/2002 | Lacey |
| 6,674,836 B2 | 1/2004 | Harada et al. |
| 7,197,113 B1 | 3/2007 | Katcha et al. |
| 7,634,046 B2 * | 12/2009 | Krumme .............. A61B 6/56 378/101 |
| 7,848,482 B2 | 12/2010 | Nakayama et al. |
| 8,172,460 B2 | 5/2012 | Ren et al. |
| 8,824,624 B2 | 9/2014 | Loef et al. |
| 8,987,944 B2 | 3/2015 | Friesner et al. |
| 2001/0008552 A1 | 7/2001 | Harada et al. |
| 2006/0022785 A1 * | 2/2006 | Dobbs .............. A61B 6/56 336/120 |
| 2006/0202650 A1 | 9/2006 | Hausner et al. |
| 2009/0116618 A1 * | 5/2009 | Nakayama ........... A61B 6/035 378/107 |
| 2012/0265050 A1 | 10/2012 | Wang |
| 2014/0003583 A1 * | 1/2014 | Krupica ............... H05G 1/10 378/101 |
| 2014/0010343 A1 | 1/2014 | Basu et al. |
| 2014/0239715 A1 * | 8/2014 | Weedon .............. A61B 6/56 307/17 |
| 2015/0207415 A1 | 7/2015 | Caiafa et al. |
| 2016/0127052 A1 * | 5/2016 | Steffens ............. H04B 5/0031 455/67.14 |
| 2016/0181791 A1 * | 6/2016 | Herrmann ........... H02H 7/1225 378/104 |

* cited by examiner

OPEN DRUM GANTRY FOR COMPUTED TOMOGRAPHY SYSTEM

BACKGROUND

The field of the disclosure relates generally to computed tomography (CT) systems and, more particularly, to an open drum gantry for a gantry CT system.

Generally, CT gantry systems include a stationary portion, referred to as a stator, and a gantry that rotates about the stator. The gantry houses X-ray source and X-ray detector components. The stator delivers power through a slip ring to the gantry to operate the CT gantry system.

Power for operating the CT gantry system can be transmitted from the stator to the gantry using various techniques. One technique utilizes contact slip rings that establish a mechanical conductive bridge between the stator and gantry. The mechanical conductive bridge is typically formed by a sliding contact, such as, for example, a conductive brush. Alternatively, a non-contacting slip ring may be utilized, referred to as a rotary transformer. The rotary transformer utilizes high-frequency electromagnetic fields to couple the stator to the gantry for power transmission.

BRIEF DESCRIPTION

In one aspect, a gantry rail for a gantry computed tomography (CT) system is provided. The gantry rail includes a secondary side of a rotary transformer and an annular body having an annular rolling surface and an annular slip ring surface. The annular body is aligned orthogonal to a longitudinal axis of the gantry CT system. The annular rolling surface has a normal vector that extends radially outward and orthogonal to the longitudinal axis. The annular slip ring surface defines a plane orthogonal to the longitudinal axis, and includes a slot disposed in the slip ring surface. The slot is configured to engage the secondary side of the rotary transformer.

In another aspect, a method of operating a gantry CT system is provided. The method includes powering an X-ray source and an X-ray detector on an open drum gantry using a secondary side of a rotary transformer. The secondary side is disposed in a slot of a slip ring surface of a gantry rail of the open drum gantry. The method further includes transmitting an X-ray signal through an interior of the open drum gantry toward the X-ray detector. The method further includes rotating the open drum gantry using a bearing engaging a roller surface of the gantry rail.

In yet another aspect, an open drum gantry for a gantry CT system is provided. The open drum gantry includes an X-ray source, an X-ray detector, a secondary side of a rotary transformer, and a gantry rail. The X-ray source is configured to transmit an X-ray signal through an interior of the open drum gantry. The X-ray detector is configured to receive the X-ray signal. The secondary side of the rotary transformer is configured to provide power to the X-ray source and the X-ray detector. The gantry rail is disposed at a first end of the open drum gantry. The gantry rail includes an annular rolling surface and an annular slip ring surface. The annular rolling surface is configured to engage a bearing to support the open drum gantry. The annular slip ring surface includes a slot to engage the secondary side of the rotary transformer.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, a number of terms are referenced that have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged. Such ranges are identified and include all the sub-ranges contained therein unless context or language indicates otherwise.

Contact slip ring devices are subject to wear and require frequent maintenance or replacement. Moreover, the sliding action causes the brushes to abrade and introduce particulate contamination into the system. Alternatively, a non-contact slip ring, or rotary transformer, may be utilized in gantry CT systems. Non-contact slip rings require small gaps between the two components of the slip ring to efficiently transmit power. The gaps may range from 0.5 to 5 millimeters and generally require co-planarity of the two surfaces of the two slip ring components. It is realized herein that manufacturing and assembling such a non-contact slip ring for gantry CT systems is typically expensive and, moreover, maintaining the gap over the entire slip ring can be difficult.

Figure 1:
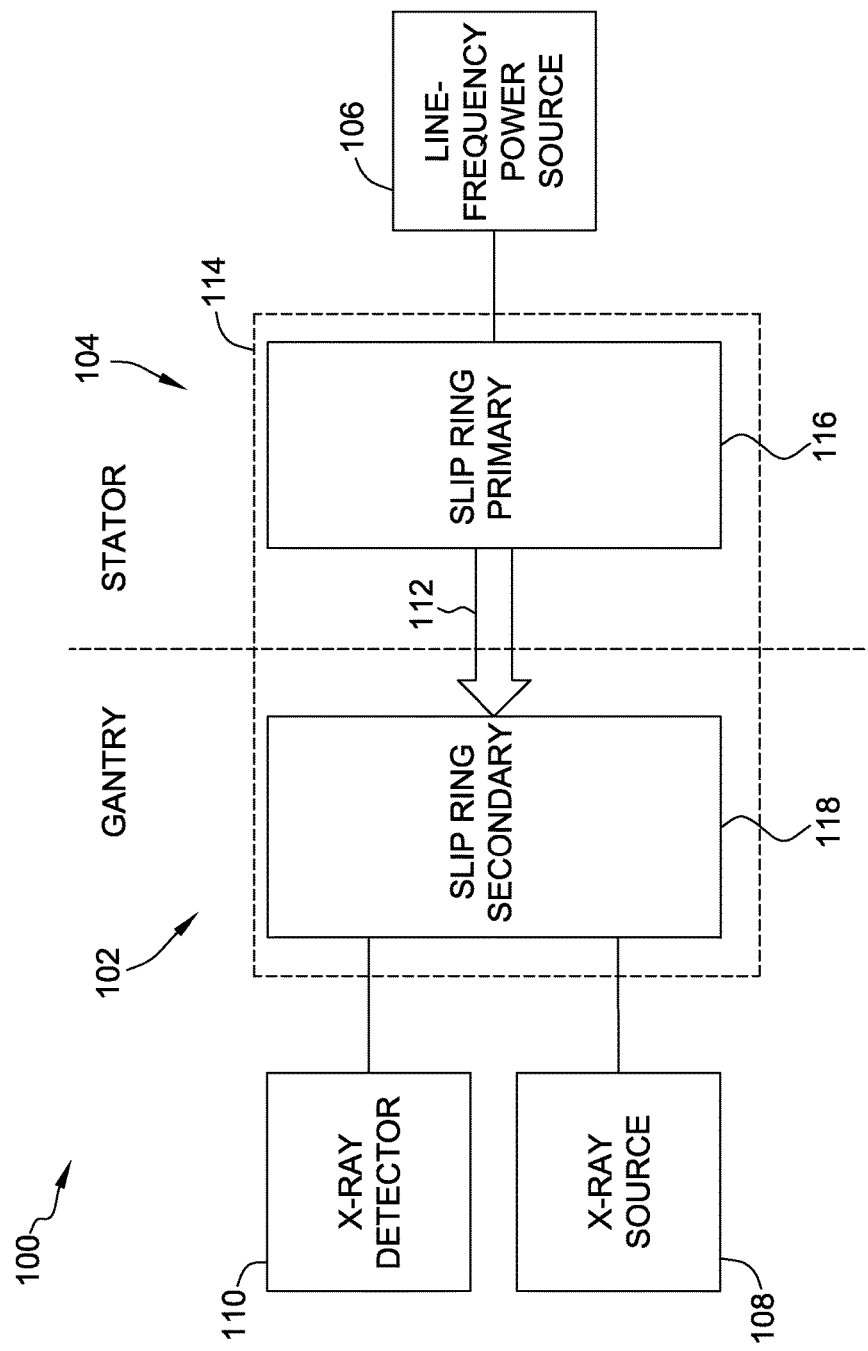
FIG. 1 is a block diagram of an exemplary gantry CT system.

FIG. 1 is a block diagram of an exemplary gantry CT system 100 having a gantry 102 and a stator 104. Stator 104 includes stationary components of gantry CT system 100, including a line-frequency power source 106 that powers gantry CT system 100. Gantry 102 is rotatably coupled to stator 104, facilitating gantry 102 and its components turning about stator 104. Gantry 102 includes an X-ray source 108 and an X-ray detector 110. X-ray source 108 generates X-ray signals that are used by gantry CT system 100 to interrogate an object. X-ray detector 110 detects the generated X-ray signals as they pass through, pass by, reflect, deflect, or otherwise interact with the object being interrogated.

X-ray source 108 and X-ray detector 110 require power to operate. Generally, components of gantry 102, such as X-ray source 108 and X-ray detector 110, utilize DC or line-frequency AC gantry power 112. Due to the rotating relationship between gantry 102 and stator 104, gantry power 112 is delivered from stator 104 to gantry 102 through a slip ring 114. Slip ring 114 provides an electrical connection between stator 104 and gantry 102 using a primary ring 116 and a secondary ring 118. Generally, a slip ring provides such an electrical connection using a contact connection or a non-contact connection, such slip rings respectively referred to as contact slip rings and non-contact slip rings. In the exemplary embodiment of FIG. 1, slip ring 114 is a non-contact slip ring utilizing a rotary transformer to transmit gantry power 112 from primary ring 116 to secondary ring 118.

Figure 2:
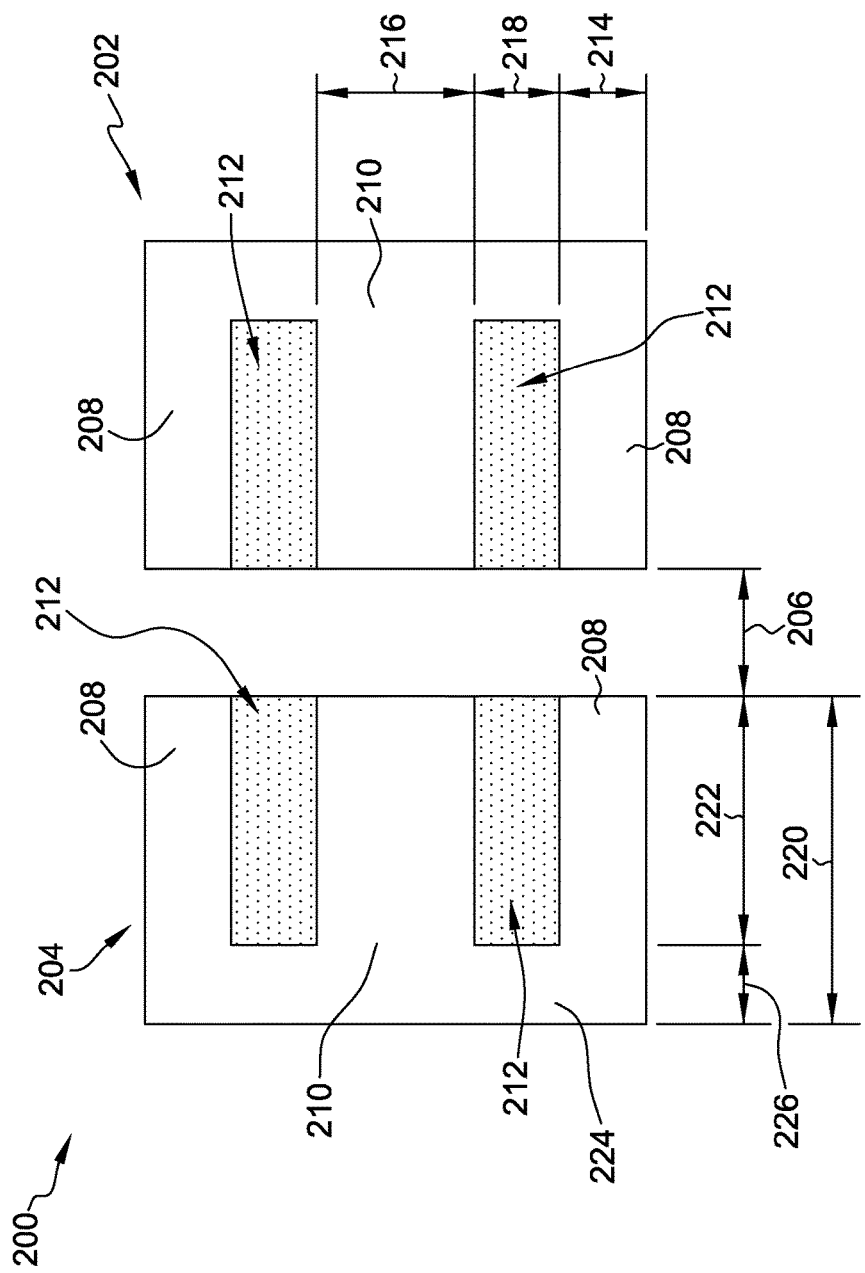
FIG. 2 is a cross-sectional diagram of an exemplary core for a rotary transformer for use in the gantry CT system shown in FIG. 1.

FIG. 2 is a cross-sectional diagram of an exemplary core 200 for a rotary transformer for use in gantry CT system 100 (shown in FIG. 1). Core 200 includes a primary core 202 and a secondary core 204. Primary core 202 and secondary core 204 are separated by an air gap 206. Core 200 is preferably manufactured of a material having high relative permeability, such as, for example, silicon steel, Metglas, Iron, Permalloy, ferrite materials or other suitable material. Core 200 includes side posts 208 and a center post 210. Side posts 208 are separated from center post 210 by air gaps 212, all of which are arranged in the form of the letter "E.". Side posts 208 have a side post width 214 of 1 unit, while center post 210 has a center post width 216 of 2 units. Air gaps 212 separating side posts 208 and center post 210 have a gap width 218 of 1 unit. Core 200 has a total length 220 of 4 units. Of total length 220, side posts 208 and center post 210 have post lengths 222 of 3 units, while a backplane 224 has a backplane length 226 of 1 unit. The precise dimensions of core 200 are scalable as each implementation requires and are largely dependent on power requirements. The ratios among the various dimensions are chosen at least partially to simplify manufacturing of E-core laminates.

Figure 3:
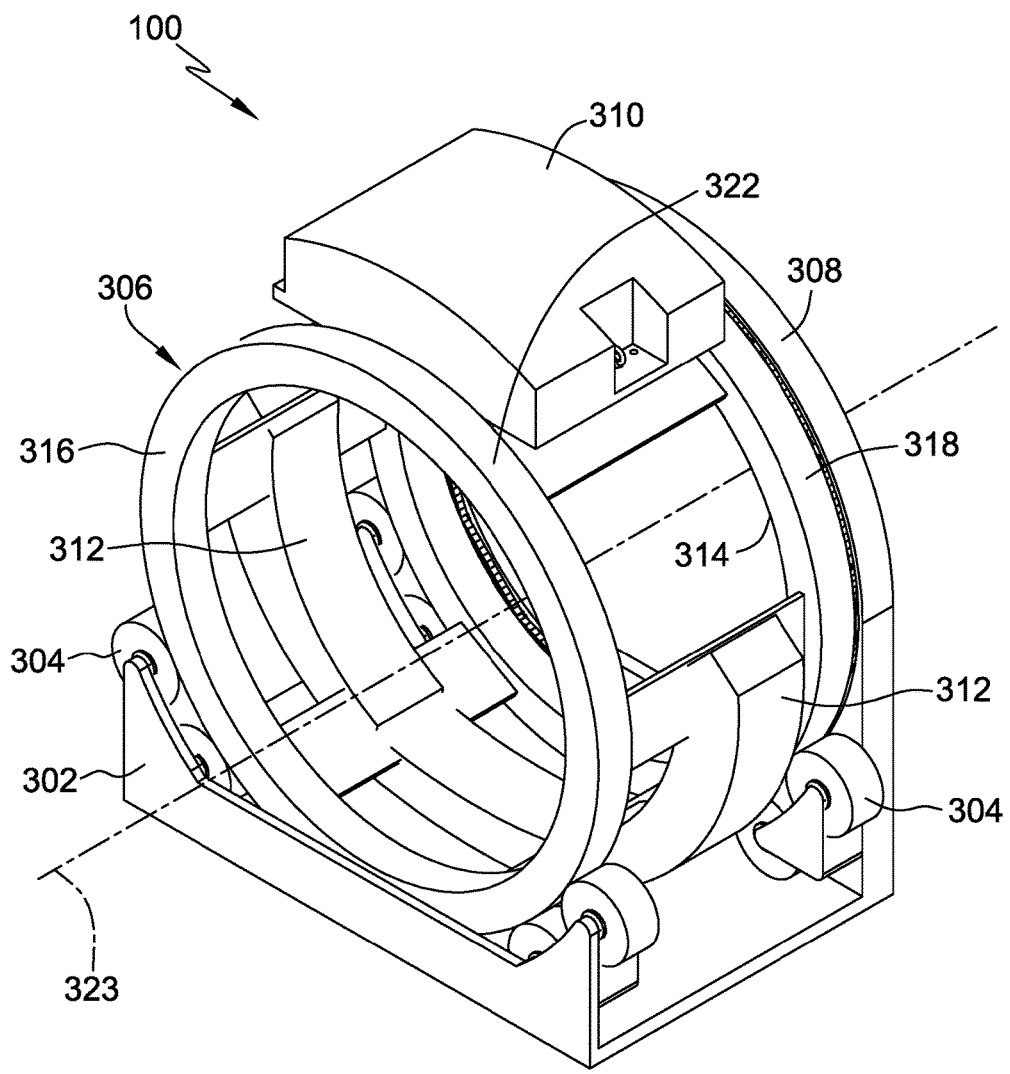
FIG. 3 is a perspective view of an the gantry CT system shown in FIG. 1.
Figure 4:
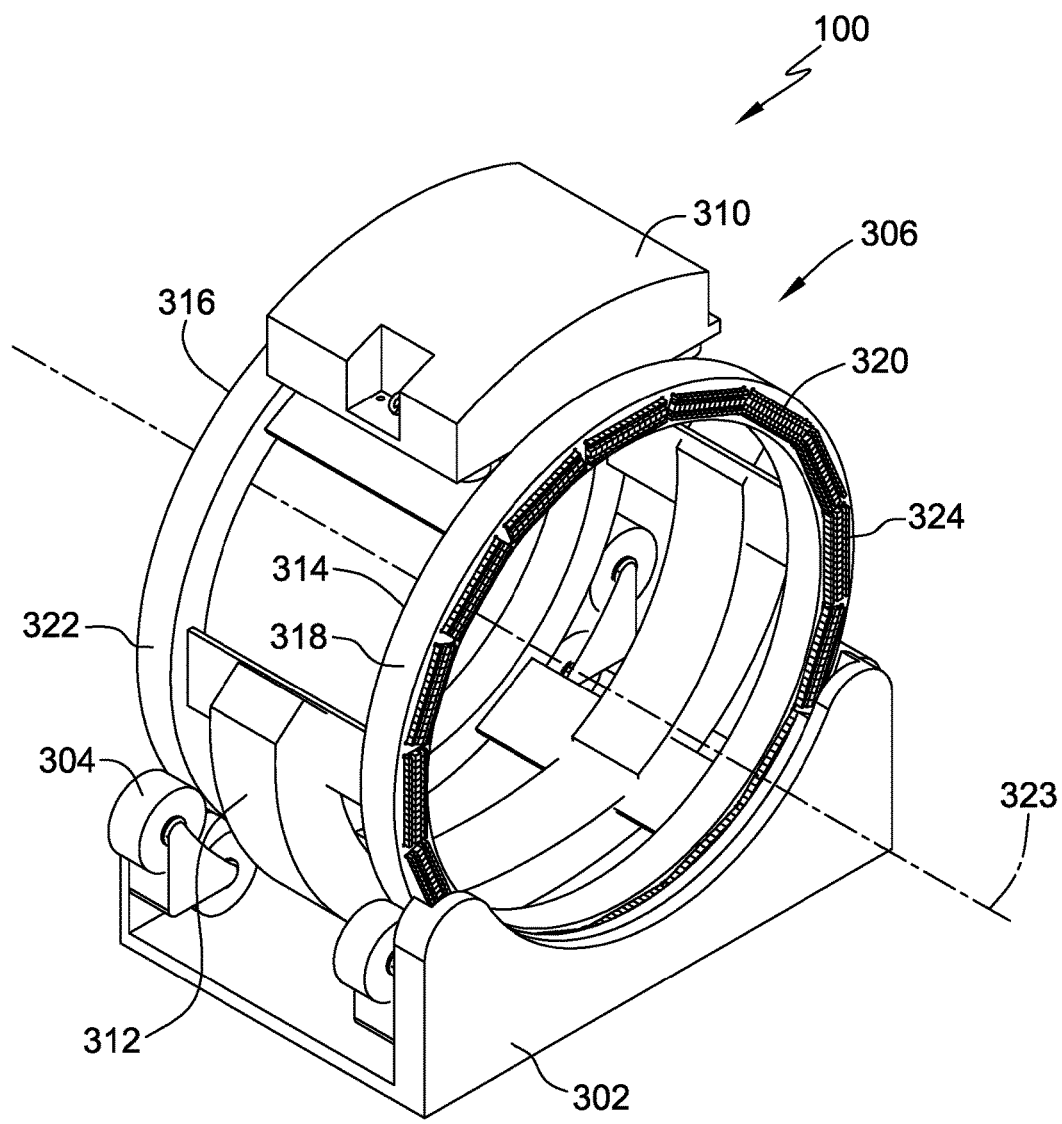
FIG. 4 is another perspective view of the gantry CT system shown in FIG. 1.

FIGS. 3 and 4 are perspective views of gantry CT system 100 (shown in FIG. 1). Gantry system 100 includes a base frame 302 onto which rollers 304 are mounted. Rollers 304 support an open drum gantry 306. Open drum gantry 306 is configured to rotate on rollers 304. Gantry CT system 100 further includes a stator 308 mounted to base frame 302. Stator 308 includes a primary side of a rotary transformer, such as primary core 202 (shown in FIG. 2), configured to transmit power from stator 308 to gantry 306. In FIG. 4, stator 308 is removed for clarity.

Open drum gantry 306 includes an X-ray source 310 and an X-ray detector 312. X-ray source 310 is configured to transmit an X-ray signal through an interior of open drum gantry 306 toward X-ray detector 312. Open drum gantry 306 further includes a first gantry rail 314 and a second gantry rail 316. First gantry rail 314 and second gantry rail 316 are disposed on opposite ends of open drum gantry 306. First gantry rail 314 includes a roller surface 318 and a slip ring surface 320. Second gantry rail 316 includes a roller surface 322. First and second gantry rails 314 and 316 are aligned with a longitudinal axis 323 of gantry CT system 100.

Slip ring surface 320 includes a slot (not shown) configured to engage a secondary side 324 of the rotary transformer. Secondary side 324 of the rotary transformer includes a secondary core and a secondary winding, such as secondary core 204 (shown in FIG. 2). Secondary side 324 is configured to receive power at open drum gantry 306 transmitted from stator 308 and the primary side of the rotary transformer. Secondary side 324 includes multiple arc-sections arranged into an annular shape. In alternative embodiments, secondary side 324 includes an annular core and winding.

Roller surface 318 and roller surface 322 are configured to engage rollers 304 such that open drum gantry 306 is rotatable about longitudinal axis 323. Roller surface 318 and roller surface 322 are further configured to support open drum gantry 306 such that air gap 206 (shown in FIG. 2) is maintained between the primary side and secondary side 324 of the rotary transformer.

Figure 5:
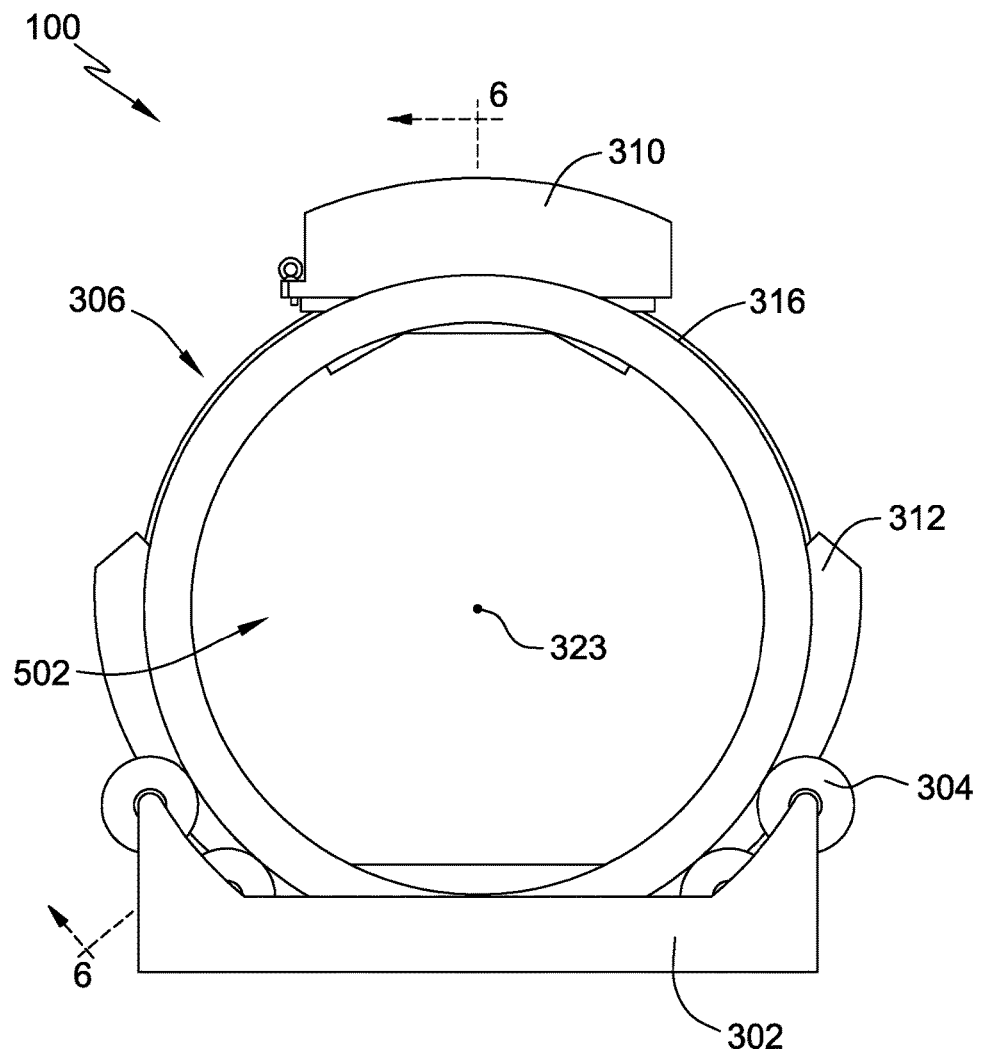
FIG. 5 is a front perspective view of the gantry CT system shown in FIGS. 3 and 4.

FIG. 5 is a front view of gantry CT system 100 (shown in FIGS. 3 and 4), including open drum gantry 306 supported by base frame 302 and rollers 304 engaging roller surface 322 of second gantry rail 316. FIG. 5 further illustrates X-ray source 310 and X-ray detector 312 mounted on open drum gantry 306. X-ray source 310 is configured to transmit the X-ray signal through an interior 502 of open drum gantry 306 toward X-ray detector 312.

Figure 6:
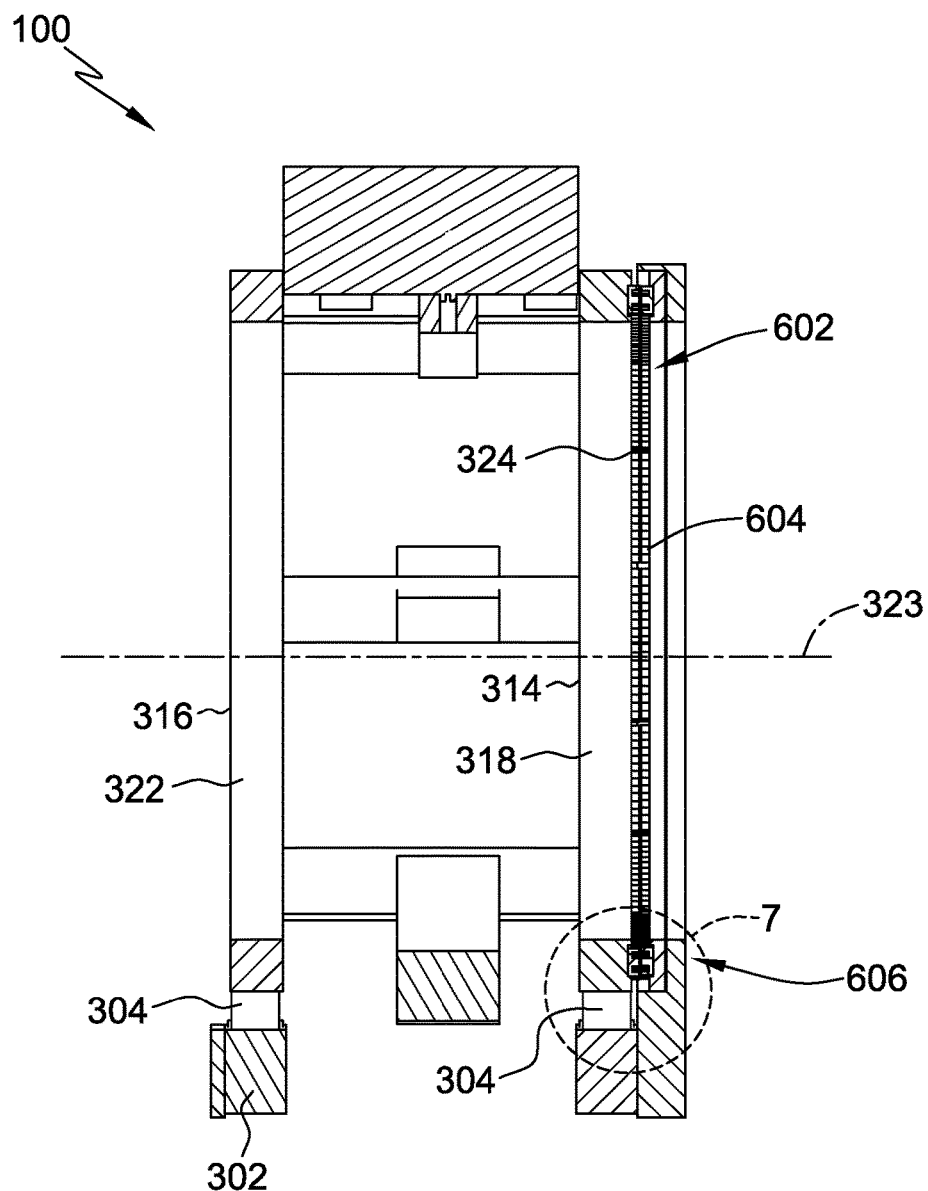
FIG. 6 is a cross-sectional diagram of the gantry CT system shown in FIGS. 3 and 4.

FIG. 6 is a cross-sectional diagram of gantry CT system 100 (shown in FIGS. 3 and 4) taken along line A-A (shown in FIG. 5). FIG. 6 illustrates rolling surface 318 of first gantry rail 314 and rolling surface 322 of second gantry rail 316. Rolling surface 318 and rolling surface 322 engage rollers 304 mounted on base frame 302.

FIG. 6 further illustrates a rotary transformer 602 having a primary side 604 and secondary side 324 (shown in FIG. 4). Rotary transformer 602 transmits power from primary side 604 on stator 308 to secondary side 324 on gantry 306.

Figure 7:
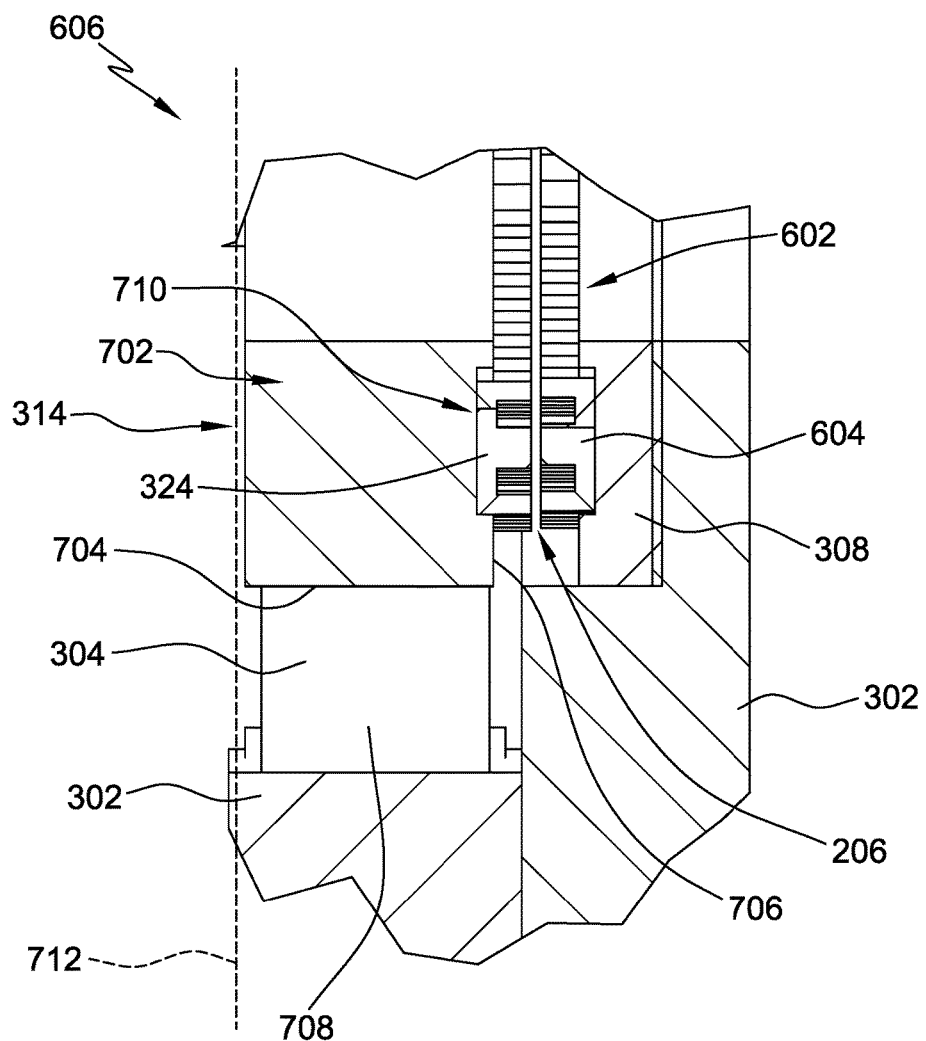
FIG. 7 is a detailed cross-sectional diagram of a gantry rail of the gantry CT system shown in FIG. 6.

FIG. 6 designates a detailed portion 606 of gantry CT system 100. FIG. 7 is an enlarged cross-sectional diagram of detailed portion 606 of gantry rail 314 of gantry CT system 100. Detailed portion 606 includes base frame 302 supporting stator 308 and primary side 604 of rotary transformer 602. Power is transmitted from primary side 604 to secondary side 324 across air gap 206.

Gantry rail 314 includes an annular body 702, a cross section of which is illustrated in FIG. 7. Annular body 702 includes an annular rolling surface 704 and an annular slip ring surface 706. In the exemplary embodiment, annular rolling surface 704 has a normal vector 708 that extends radially from annular body 702 (i.e., perpendicular to longitudinal axis 323). Annular rolling surface 704 is smooth and configured to engage roller 304 mounted on base frame 302. In other embodiments, annular rolling surface 704 may be tapered such that open drum gantry 306 centers along longitudinal axis 323 on base frame 302 as it turns on rollers 304.

Annular slip ring surface 706 includes a slot 710 that engages secondary side 324 of rotary transformer 60. Annular slip ring surface 706 is parallel to a plane 712 orthogonal to longitudinal axis 323. Slot 710, in certain embodiments, is lined with an insulating layer to galvanically isolate secondary side 324 from gantry rail 314.

Figure 8:
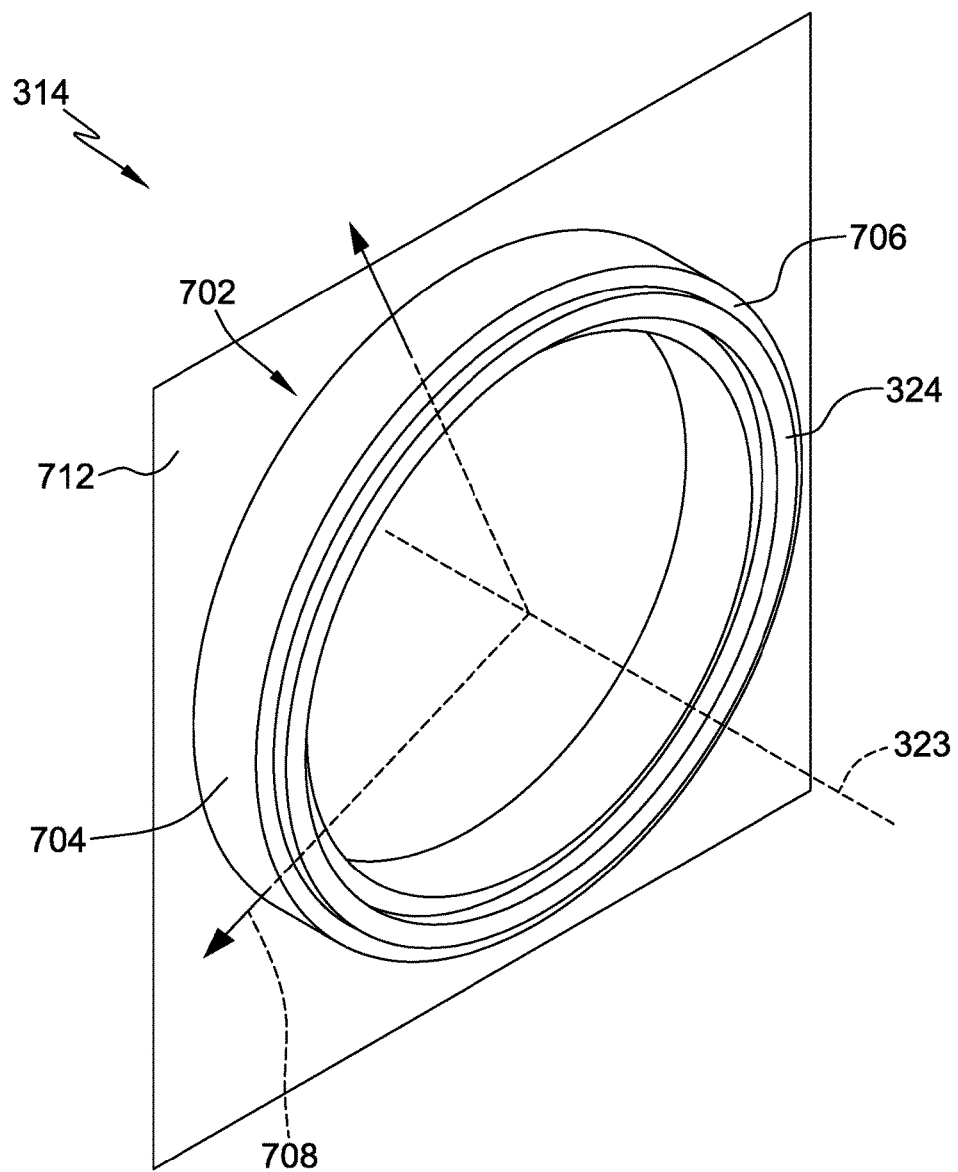
FIG. 8 is a perspective view of the gantry rail shown in FIG. 7.

FIG. 8 is a perspective view of gantry rail 314 (shown in FIG. 7) for gantry CT system 100 (shown in FIGS. 5 and 6). Annular body 702 includes annular rolling surface 704 and annular slip ring surface 706. As described above, normal vector 708 that extends radially (i.e., orthogonal to longitudinal axis 323). Annular slip ring surface 706 includes a slot (not shown), such as slot 710 (shown in FIG. 7). The slot engages secondary side 324 of rotary transformer 602. Annular slip ring surface 706 is parallel to plane 712.

In certain embodiments, secondary side 324 comprises a plurality of arc sections rather than a contiguous annular core. In such embodiments, the slot in annular slip ring surface 706 can be a contiguous slot to engage the plurality of arc sections of secondary side 324, or can include arc-section slots respectively configured to engage the plurality of arc-section cores of secondary side 324.

Figure 9:
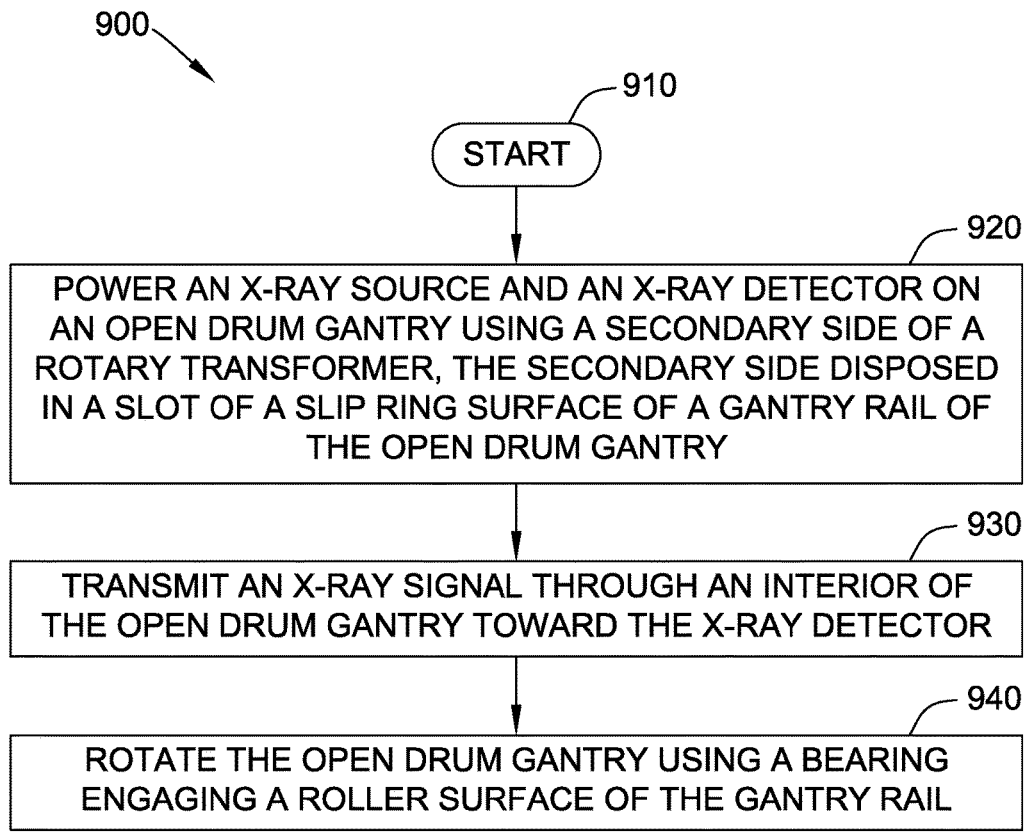
FIG. 9 is a flow diagram of an exemplary method of operating the gantry CT system shown in FIGS. 1-8.

FIG. 9 is a flow diagram of an exemplary method 900 of operating gantry CT system 100 (shown in FIGS. 1-8). Method 900 begins at a start step 910. At a powering step 920, X-ray source 310 and X-ray sensor 312 on open drum gantry 306 (shown in FIG. 3) are powered through rotary transformer 602. Power is transmitted from primary side 604 to secondary side 324 (all shown in FIG. 6). Secondary side 324 is disposed in slot 710 on slip ring surface 706 of gantry rail 314 (all shown in FIG. 7).

At a scan step 930, X-ray source 310 transmits an X-ray signal through interior 502 of open drum gantry 306 toward X-ray detector 312. Open drum gantry 306 rotates about interior 502 at a rotating step 940. Open drum gantry 306 rotates using respective rolling surfaces 318 and 322 of first gantry rail 314 and second gantry rail 316 to bearings, such as rollers 304. The method ends at an end step 950.

An exemplary technical effect of the methods, systems, and apparatus described herein includes at least one of: (a) integrating a rolling surface and a secondary side of a rotary transformer into a single gantry rail component; (b) simplifying manufacture of an open drum gantry through integration of the rolling surface and rotary transformer; (c) providing a smooth machined surface on a gantry rail for engaging rollers; and (d) maintaining a precise air gap between primary and secondary sides of the rotary transformer utilizing the smooth machine surface for rolling.

Exemplary embodiments of methods, systems, and apparatus for open drum gantries are not limited to the specific embodiments described herein, but rather, components of systems and/or steps of the methods may be utilized independently and separately from other components and/or steps described herein. For example, the methods may also be used in combination with other non-conventional open drum gantries, and are not limited to practice with only the systems and methods as described herein. Rather, the exemplary embodiment can be implemented and utilized in connection with many other applications, equipment, and systems that may benefit from increased efficiency, reduced operational cost, and reduced capital expenditure.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gantry rail for a gantry computed tomography (CT) system, said gantry rail comprising:
   a secondary side of a rotary transformer configured to receive line-frequency power from a primary side of the rotary transformer; and
   an annular body aligned orthogonal to a longitudinal axis of the gantry CT system, said annular body comprising:
   an annular rolling surface having a normal vector extending radially outward and orthogonal to the longitudinal axis,
   an annular slip ring surface defining a plane orthogonal to the longitudinal axis, and
   a slot disposed in said slip ring surface and configured to engage said secondary side.

2. The gantry rail of claim 1, wherein said secondary side comprises an E-core and a secondary winding.

3. The gantry rail of claim 1 further comprising an electrical insulator layer lining said slot to galvanically isolate said secondary side of said rotary transformer from said annular body.

4. The gantry rail of claim 1, wherein said annular rolling surface is configured to engage a bearing couplable to a base frame of said gantry CT system.

5. The gantry rail of claim 1, wherein said slot comprises an annular slot.

6. The gantry rail of claim 1, wherein said annular body further comprises a plurality of arc-section slots disposed in said slip ring surface and configured to engage said secondary side.

7. The gantry rail of claim 1, wherein said annular body has a rectangular cross-section.

8. A method of operating a gantry computed tomography (CT) system, said method comprising:
   powering a primary side of a rotary transformer using a line-frequency power source;
   powering an X-ray source and an X-ray detector on an open drum gantry using a secondary side of the rotary transformer, the secondary side magnetically couplable to the primary side and disposed in a slot of a slip ring surface of a gantry rail of the open drum gantry;
   transmitting an X-ray signal through an interior of the open drum gantry toward the X-ray detector; and
   rotating the open drum gantry using a bearing engaging a roller surface of the gantry rail.

9. The method of claim 8 further comprising engaging a second bearing on a second rolling surface of a second gantry rail disposed on the open drum gantry.

10. The method of claim 8 further comprising maintaining an air gap between the secondary side of the rotary transformer and a primary side of the rotary transformer, the primary side coupled to a stator of the gantry CT system.

11. The method of claim 8 further comprising galvanically isolating the secondary side of the rotary transformer from the gantry rail.

12. The method of claim 8, wherein engaging the roller surface of the gantry rail using a bearing comprises engaging a roller mounted on a base frame of the gantry CT system.

13. The method of claim 8, wherein powering the X-ray source and the X-ray detector using the secondary side of the rotary transformer comprises:
applying power to a primary side of the rotary transformer;
electromagnetically coupling the primary side to the secondary side of the rotary transformer; and
delivering power to the X-ray source and the X-ray detector.

14. The method of claim 8 further comprising centering the open drum gantry on a base frame of the gantry CT system using a taper on the roller surface of the gantry rail.

15. An open drum gantry for a gantry computed tomography (CT) system, said open drum gantry comprising:
an X-ray source configured to transmit an X-ray signal through an interior of said open drum gantry;
an X-ray detector configured to receive the X-ray signal;
a secondary side of a rotary transformer configured to provide power to said X-ray source and said X-ray detector, wherein said secondary side of said rotary transformer is magnetically couplable to a primary side of said rotary transformer and said primary side is connected to a line-frequency power source;
a first gantry rail disposed at a first end of said open drum gantry, comprising:
an annular rolling surface configured to engage a bearing to support said open drum gantry, and
an annular slip ring surface comprising a slot to engage said secondary side of said rotary transformer.

16. The open drum gantry of claim 15, wherein said annular rolling surface is tapered to facilitate centering of said open drum gantry as said annular rolling surface engages said bearing.

17. The open drum gantry of claim 15, further comprising a second gantry rail disposed at a second end of said open drum gantry, said second end opposite said first end, said second gantry rail comprising a second annular rolling surface configured to engage a second bearing to support said open drum gantry.

18. The open drum gantry of claim 15, wherein said primary side of said rotary transformer is fixed to a stator of said gantry CT system.

19. The open drum gantry of claim 18, wherein said annular rolling surface comprises a machined surface configured to maintain an air gap between said primary side and said secondary side of said rotary transformer.

* * * * *